United States Patent [19]

Hope

[11] Patent Number: Plant 5,384

[45] Date of Patent: Jan. 8, 1985

[54] KALANCHOE PLANT NAMED "ACAPULCO"

[75] Inventor: Claude Hope, Cartago, Costa Rica

[73] Assignee: Pan American Plant Company, Parrish, Fla.

[21] Appl. No.: 496,283

[22] Filed: May 19, 1983

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new and distinct cultivar of Kalanchoe plant named Acapulco characterized by its bright and uniform fuchsia flower color, compact habit, freely branching, with shoots formed at every node, highly floriferous habit, and by its suitability for production in 10 to 15 cm. pots.

1 Drawing Figure

The present invention relates to a new and distinctive cultivar of Kalanchoe plant, botanically known as Kalanchoe, and referred to by the cultivar name Acapulco.

The new cultivar was referred to during the selection process by the designation [(Melody-4-1 × Red Empress-3-1)-2-3-17] × Swiss Rose-9-6-4-3-2]-1-1, and is a product of a planned breeding program. Acapulco was later recoded KLV80-22P when received by Pan American Plant Company in West Chicago, Ill. in 1980. The basic objective of the breeding program was to create a new Kalanchoe cultivar having brilliant fuchsia flower color, compact habit, and the ability to produce commercially acceptable quality in a year-round Kalanchoe program.

The new cultivar was originated from a self-pollination of [(Melody-4-1 × Red Empress-3-1)-2-3-17] × Swiss Rose-9-6-4-3-2]-1, made in a controlled breeding program at Linda Vista S.A., Cartago, Costa Rica.

Acapulco was discovered and selected by me as a flowering plant within the progeny of the stated self in a field of seedlings in Cartago, Costa Rica. Asexual reproduction of the new cultivar by stem cuttings, as first performed by me at Cartago, Costa Rica, and subsequently performed in West Chicago, Ill., and Parrish, Fla., has demonstrated that the combination of characteristics as herein disclosed for the new cultivar are firmly fixed and are retained through successive generations of asexual reproduction.

Acapulco has not been observed under all possible environmental conditions. The phenotype may vary significantly with variations in environment such as temperature, light intensity and day length. The following observations measurements and values describe the new cultivar as grown in Parrish, Fla., under greenhouse conditions which closely approximate those generally used in commercial practice.

The following traits have been repeatedly observed and are determined to be basic characteristics of Acapulco, which in combination distinguish this Kalanchoe as a new and distinct cultivar:

1. Outstanding bright and uniform fuchsia flower color.

2. Compact habit; average growth rate as compared to other commercial cultivars.

3. Freely branching, with shoots formed at every node.

4. Suitable for production in 10 to 15 cm. pots, flowering from 11 weeks in summer to 14 weeks in the winter.

5. Highly floriferous, with numerous flowers formed at every shoot.

6. To reduce peduncle elongation after flower initiations, plants can be treated with B-9.

The new cultivar is most similar to Sensation, disclosed in U.S. Plant Pat. No. 4,727. Acapulco is principally distinguished from Sensation by its smaller leaf size, somewhat more purple flower color, and the uniformity of flower color.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under natural light conditions at approximately 4:00 P.M. in Parrish, Fla.

BOTANICAL CLASSIFICATION

Kalanchoe, cv. Acapulco.

PARENTAGE

Self-pollination of [(Melody-4-1×Red Empress 3-1)-2-3-17] × Swiss Rose-9-6-4-3-2]-1.

PROPAGATION

The new cultivar holds its distinguishing characteristics through successive propagations by leaf cuttings and by division of shoots.

Type cutting: Tip cuttings with stems up to 2cm. long.

Time to root: 10 Days at 21° C. summer, 14 days at 21° C. winter.

Rooting habit: Fibrous, many very fine roots.

PLANT DESCRIPTION

Form: Upright, short, compact. Growing and scheduling practices can produce small plants in 10 cm. pots or large plants in 15 cm. pots.

Habit of growth: Average growth rate for this type of plant. Generally, shoots are formed at every node.

Foliage description: Leaves simple, opposite, generally symmetrical.

1. *Size.*—Average size of full grown leaf of a flowering plant in a 10 cm. pot is 50–70 mm. long and 35(14 50 mm. wide. Plants in larger pots have proportionately larger leaves.

2. *Shape.*—Ovate, apex acute to obtuse, base truncate.

(b 3. *Texture.*—Glabrous, coriaceous, succulent.

4. *Margin.*—Crenate.

5. *Color.*—Young foliage top side, 147A, under side, 147B. Mature foliage top side 147A, under side 147B.

FLOWERING DESCRIPTION

Flowering habit: Inflorescence of each shoot is formed by dichotomous branching, starting with opening of terminal flower at main axis followed by terminal flowers of the side branches of the inflorescence. Opening of new buds will continue for 2 months or more. Individual flowers last 2 weeks or more after opening.

Natural flowering season is January. Flowering time under controlled day length at 30° C. in summer is 10 weeks; in winter at 20° C., 13 weeks. Flowering time depends on temperature, light intensity and other growing conditions.

Flower buds: Oblong, developing to tubular as petals mature, sheathed with four green sepals; corolla at maturity about 13 mm. long.

1. *Size.*—15 mm. long.
2. *Shape.*—Oblong.
3. *Rate of opening.*—Normal.

Flowers borne: Compound dichasial cyme on strong peduncles. Peduncle length depends on growing conditions and B-9 applications. Pedicles up to 5 mm. long.

Quantity of flowers: Very floriferous, with new buds continuing to develop.

Petals:

1. *Shape.*—Nearly round, apex cuspidate.
2. *Color.*—Top side when opening 63A, fading to 67B; under side 63B.
3. *Number and size of petals.*—Four, united in corolla, 7 mm. in diameter; total flower diameter 16 mm.

Reproductive organs:

1. *Stamen.*—8 In number (a) Anther shape: Flat, elliptical. (b) Filament color: Yellow. (c) Pollen color: yellow.
2. *Pistels.*—(a) Stigma shape: Flat, crystalline. (b) Style color: Greenish-white. (c) Ovaries: 4 celled, 7 mm. long, green.

DISEASE RESISTANCE

No known Kalanchoe diseases observed to date.

I claim:

1. A new and distinct cultivar of Kalanchoe plant named Acapulco, as described and illustrated, and particularly characterized by its bright and uniform fuchsia flower color; compact habit; freely branching, with shoots formed at every node; highly floriferous habit, and by its suitability for production in 10 to 15 cm. pots.

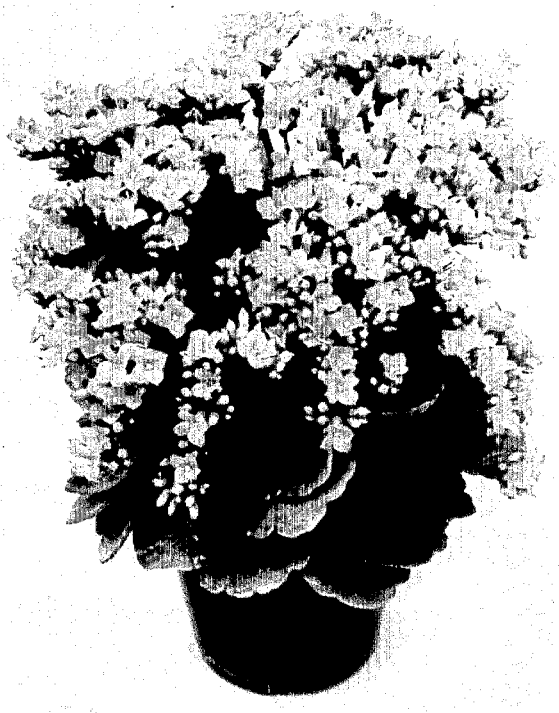

* * * * *